United States Patent
Haugaard et al.

(10) Patent No.: US 11,432,793 B2
(45) Date of Patent: Sep. 6, 2022

(54) HIGH RESOLUTION COMPOUND ULTRASOUND FLOW IMAGING

(71) Applicant: B-K Medical Aps, Herlev (DK)

(72) Inventors: Per Haugaard, Skovlunde (DK); Gert Seerup, Hilleroed (DK)

(73) Assignee: BK Medical Aps, Herlev (DK)

( * ) Notice: Subject to any disclaimer, the term of this patent is extended or adjusted under 35 U.S.C. 154(b) by 1027 days.

(21) Appl. No.: 16/065,235

(22) PCT Filed: Dec. 28, 2015

(86) PCT No.: PCT/IB2015/060016
§ 371 (c)(1),
(2) Date: Jun. 22, 2018

(87) PCT Pub. No.: WO2017/115104
PCT Pub. Date: Jul. 6, 2017

(65) Prior Publication Data
US 2020/0138401 A1    May 7, 2020

(51) Int. Cl.
*A61B 8/00* (2006.01)
*A61B 8/06* (2006.01)
(Continued)

(52) U.S. Cl.
CPC .................. *A61B 8/06* (2013.01); *A61B 8/14* (2013.01); *A61B 8/4488* (2013.01);
(Continued)

(58) Field of Classification Search
CPC ....................................................... A61B 8/06
See application file for complete search history.

(56) References Cited

U.S. PATENT DOCUMENTS 6,859,659 B1    2/2005   Jensen
7,542,790 B2    6/2009   Jensen et al.
(Continued)

OTHER PUBLICATIONS

International Search Report for PCT/IB2015/060016 published as WO2017-115104 dated Jul. 6, 2017.

*Primary Examiner* — Joseph M Santos Rodriguez
(74) *Attorney, Agent, or Firm* — Daugherty & Del Zoppo Co., LPA

(57) ABSTRACT

An ultrasound imaging system includes a transducer array (202) with a plurality of transducer elements (206) configured to transmit a pulsed field beam into a scan field of view, receive echo signals produced in response to the pulsed field interacting with particles/structure flowing/moving in the scan field of view, and generate electrical signals indicative of the echo signals. The ultrasound imaging system further includes a beamformer (212) including multiple synthetic transmit aperture beamformers configured to process the electrical signals over a plurality of processing channels (312) into corresponding receive-beams of RF-data with a beam-level delay, channel-level delays, a beam-level gain and channel-level gains. The ultrasound imaging system further includes a velocity processor (216) configured to estimate a flow velocity of the structure flowing in the scan field of view from the RF-data. The ultrasound imaging system further includes a rendering engine (224) configured to display the flow velocity estimate on a display (226) with color-coding.

20 Claims, 8 Drawing Sheets

(51) Int. Cl.
*A61B 8/14* (2006.01)
*A61B 8/08* (2006.01)
*G01S 7/52* (2006.01)
*G01S 15/89* (2006.01)

(52) U.S. Cl.
CPC .......... *A61B 8/5207* (2013.01); *A61B 8/5223* (2013.01); *A61B 8/54* (2013.01); *G01S 7/5209* (2013.01); *G01S 7/52095* (2013.01); *G01S 15/8915* (2013.01); *G01S 15/8984* (2013.01); *G01S 15/8988* (2013.01); *G01S 15/8997* (2013.01); *A61B 8/488* (2013.01)

(56) References Cited

U.S. PATENT DOCUMENTS

| | | | |
|---|---|---|---|
| 2005/0043622 A1* | 2/2005 | Jensen | G01S 15/8915 600/449 |
| 2014/0257103 A1* | 9/2014 | Jensen | A61B 8/4488 600/441 |

* cited by examiner

HIGH RESOLUTION COMPOUND ULTRASOUND FLOW IMAGING

RELATED APPLICATION

This application is a national filing of PCT application Serial No. PCT/IB2015/060016, filed Dec. 28, 2015, published as WO2017/0115104 on Jul. 6, 2017. This application claims priority to PCT application Serial No. PCT/IB2015/060016, published as WO2017/0115104 on Jul. 6, 2017.

TECHNICAL FIELD

The following generally relates to ultrasound imaging and more particularly to color flow imaging.

BACKGROUND

Ultrasound imaging provides a real-time image with information about the interior of a subject such as organs and blood vessels. In addition, ultrasound imaging can visualize flow inside blood vessels in real-time. Conventional Color Flow Mapping (CFM) is one approach to estimate and visualize the flow inside blood vessels. The CFM is typically super-imposed on top of a black-and-white (B-mode) image that shows the tissue structures. CFM can be realized efficiently and made feasible using a low-cost velocity estimator. CFM imaging has typically been limited to smaller region of interest (ROI) of the whole image view relative to the B-mode image in order to achieve high spatial resolution and frame-rates. Increasing the ROI and/or the frame rate while maintaining high spatial resolution requires acquisition of more data per displayed image frame, and acquiring more data per frame requires longer acquisition times and hence lower display frame rates.

To address the above, parallel data-acquisition is deployed, in which data is acquired for several image lines per acquisition event (shot). An ultrasound acquisition event is an emission of an ultrasound wave followed by the reception of multi-channel echo-signals and beamforming of these into beams of RF-data. Each beam is processed by the velocity processor into a scan-line of velocity estimates and processed by the rendering unit into an image-line for the final displayed image. In parallel data acquisition, multiple beam-formers are employed, forming a block of multiple receive beams per acquisition event. However, mapping the blocks of receive beams to image-lines for the final image is an issue. A direct mapping of receive beams of RF-data to scan-lines of velocity-estimates to image-lines will produce flow images with severe block-artifacts. Applying a lateral averaging filter to reduce the artifacts will also reduce the lateral spatial resolution.

An example of an acquisition sequence of prior art high spatial resolution color flow systems is illustrated in FIG. 1. The acquisition sequence for a whole display image is to acquire a first frame with transmit beams {0, 4} and receive beams {−1, 0, 1, . . . 6}, a second frame with transmit beams {1, 5} and receive beams {0, . . . 7}, a third frame with transmit beams {2, 6} and receive beams {1, . . . 8}, and a firth frame with transmit beams {3, 7} and receive beams {2, . . . 9}. Where the aligned reference frame is the second frame, the other frames are shifted laterally to acquire data using all the intermediate positions of transmit beams. This frame-based acquisition with 4 to 8 parallel receive beams works fine in some applications, but the time-lag introduced by the required de-interleaving and frame average filter makes this approach not well-suited for applications where high frame rate (fine time-resolution) is required.

SUMMARY

Aspects of the application address the above matters, and others.

In one aspect, an ultrasound imaging system includes a transducer array with a plurality of transducer elements configured to transmit a pulsed field beam into a scan field of view, receive echo signals produced in response to the pulsed field interacting with particles/structure flowing/moving in the scan field of view, and generate electrical signals indicative of the echo signals. The ultrasound imaging system further includes a beamformer including multiple synthetic transmit aperture beamformers configured to process the electrical signals over a plurality of processing channels into corresponding receive-beams of RF-data with a beam-level delay, channel-level delays, a beam-level gain and channel-level gains. The ultrasound imaging system further includes a velocity processor configured to estimate a velocity of the particles/structure flowing/moving in the scan field of view from the RF-data. The ultrasound imaging system further includes a rendering engine configured to display the flow velocity estimate on a display with color-coding.

In another aspect, a method includes transmitting, with elements of a transducer array, an ultrasound signal, receiving, with the elements of a transducer array, receives a set of echo signals generated in response to the ultrasound signal interacting with moving structure, and generating, with the elements of a transducer array, electrical signals indicative of the received set of echo signals. The method further includes acquiring, with receive circuitry, sequences of overlapping acquisition-packages. The method further includes beamforming, with multiple synthetic transmit aperture beamformers, the overlapping acquisition-packages to generate beams of RF-data. The beamforming includes channel-level delays and gains.

In another aspect, apparatus includes a transducer array that receives ultrasound echoes produced in response to a pressure field interacting with moving structure and generates analog signals indicative thereof and a console. The console includes multiple synthetic transmit aperture beamformers configured to process the analog signals using at least channel-level delays and channel-level gains and generate beamformed data. The console further includes a velocity processor configured to estimate a velocity of the moving structure flowing from the beamformed data.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following generally describes an example ultrasound imaging system configured for synthetic transmit aperture (STA) compound flow imaging, including STA compound color flow mapping (CFM) imaging, STA compound vector flow imaging (VFI), STA compound spectral velocity pulse wave Doppler (PWD) imaging, STA compound spectral vector-velocity pulse wave Doppler imaging, and/or other STA compound flow imaging.

Figure 1:
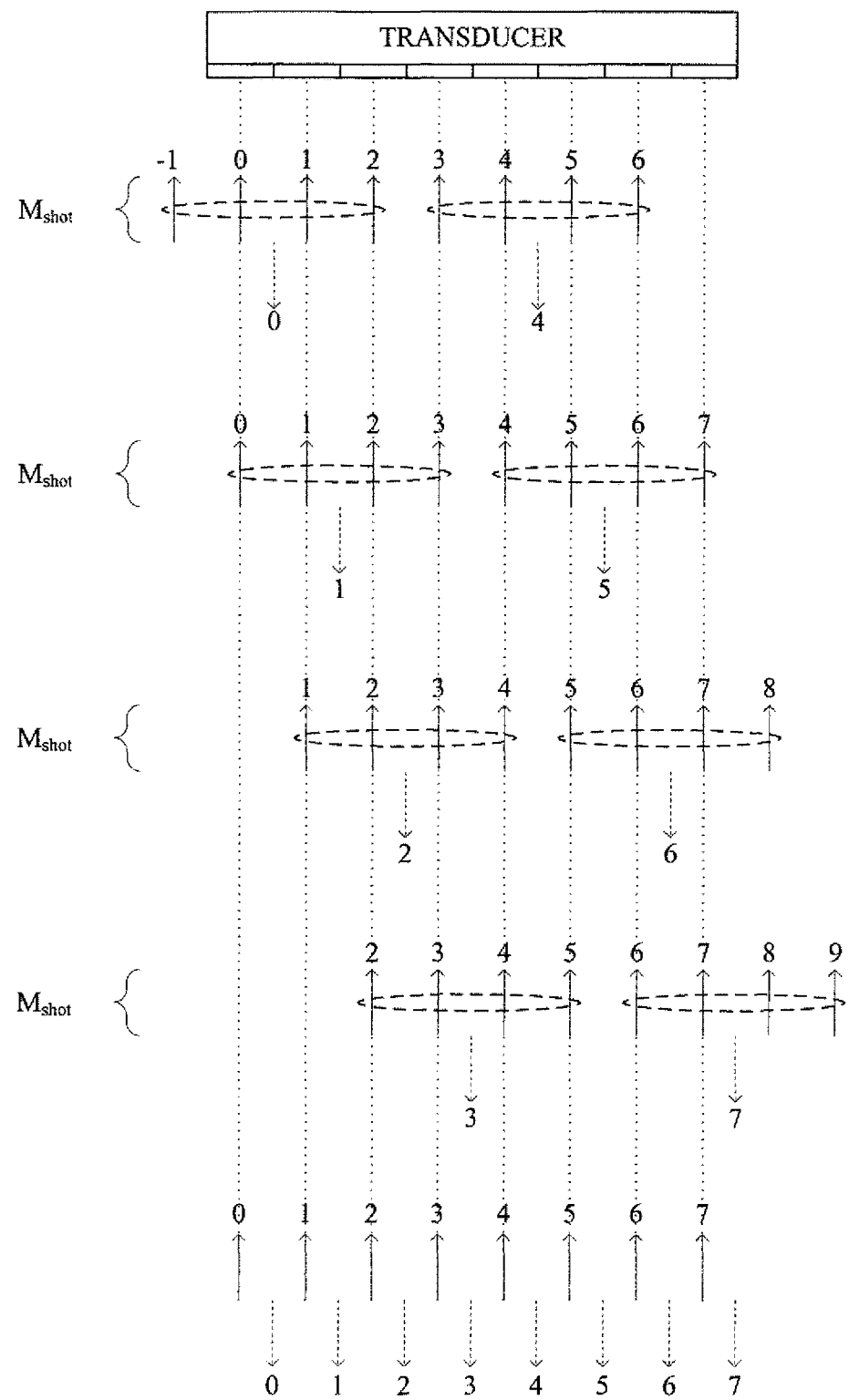
FIG. 1 schematically illustrates an acquisition sequence of a prior art high spatial resolution color flow system.
Figure 2:
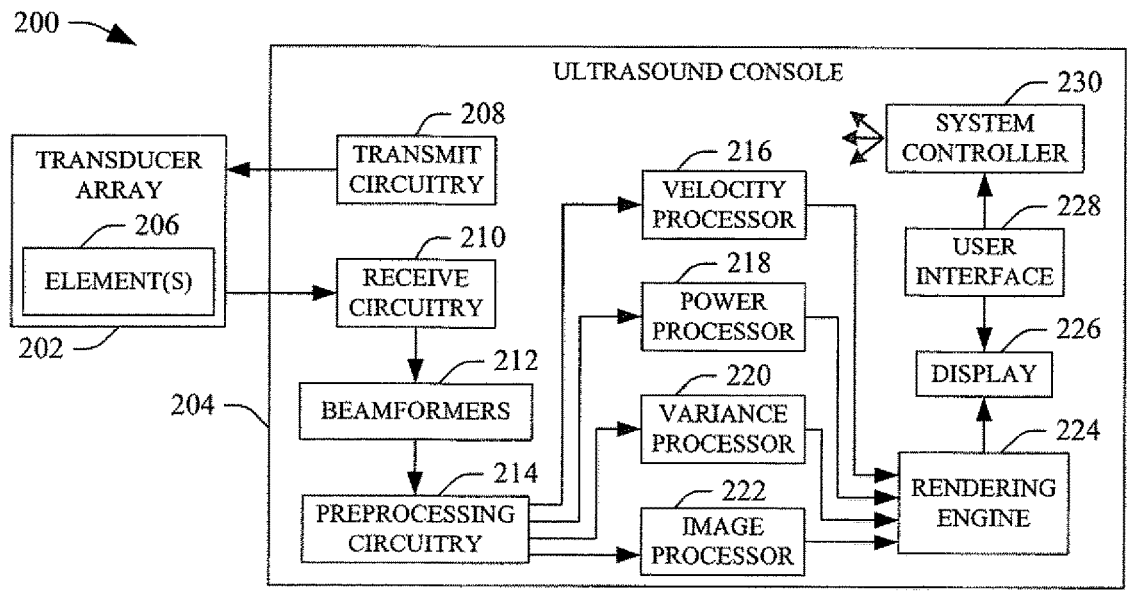
FIG. 2 schematically illustrates an example ultrasound imaging system configured for high-resolution color flow mapping.

FIG. 2 illustrates an example ultrasound imaging system 200 configured for STA compound CFM imaging. The ultrasound imaging system 200 includes a transducer array 202 and an ultrasound console 204, which interface through suitable complementary hardware and/or wireless interfaces (not visible).

The transducer array 202 includes one or more transducer elements 206. Examples of suitable arrays include 64, 128, 192, 256, and/or other elements arrays, including larger and smaller arrays. The array can be linear, curved, and/or otherwise shaped, fully populated, sparse and/or a combination thereof, etc. The one or more transducer elements 206 convert an excitation electrical signal to an ultrasound pressure field and vice versa.

The one or more transducer elements 206 can be selectively excited via the excitation electrical (pulsed) signal, which cause at least a sub-set of the transducer elements 206 to transmit an ultrasound signal into an examination or scan field of view. The ultrasound signal may be in a hard-focused ultrasound beam, a soft-focused beam, a plane wave or a defocused (spherical) wave, and/or other ultrasound signal.

The one or more transducer elements 206 also receive echo signals (ultrasound pressure field) and generate analog electrical signals indicative thereof. The echo signals, in one instance, are generated in response to the transmitted ultrasound signals interacting with structure, such as blood cells, flowing in a portion of a vessel and/or other tissue in a region of interest in the scan field of view.

Transmit circuitry 208 is configured to generate the excitation electrical signal (e.g., a predetermined number M of pulses). Receive circuitry 210 is configured to receive and condition the analog electrical signals.

A beamformer 212 is configured with multiple STA focusing beamformers. Principles of STA focused flow imaging are discussed in U.S. Pat. No. 7,542,790 B2, filed Oct. 1, 2002, and entitled "Apparatus and method for velocity estimation in synthetic aperture imaging," the entirety of which is incorporated herein by reference. The beamformer 212 may include two (2) to sixty-four (64) or more parallel beamformers, including eight (8) to sixty-four (64) or more parallel beamformers. In general, the beamformer 212 may have a scalar architecture, where a fixed compute bandwidth can form more beams in parallel at lower input samples rate than at higher rates.

The illustrated beamformer 212 includes a conventional delay-and-sum beam-former (e.g., a matched-filter beam-former, etc.). Other beamforming approaches are also contemplated herein. As described in greater detail below, the multiple STA focusing beamformers are configured with delay and gain circuitry for beam-level and channel-level delays and gains. The beamformer 212 outputs beamformed data (receive-beams of RF-data). With this configuration, the beamformer 212 mitigates any need for de-interleaving and frame average filtering and the time lag associated therewith. As such, the approach described herein is well-suited for high spatial resolution and/or high frame rate flow imaging.

Figure 3:
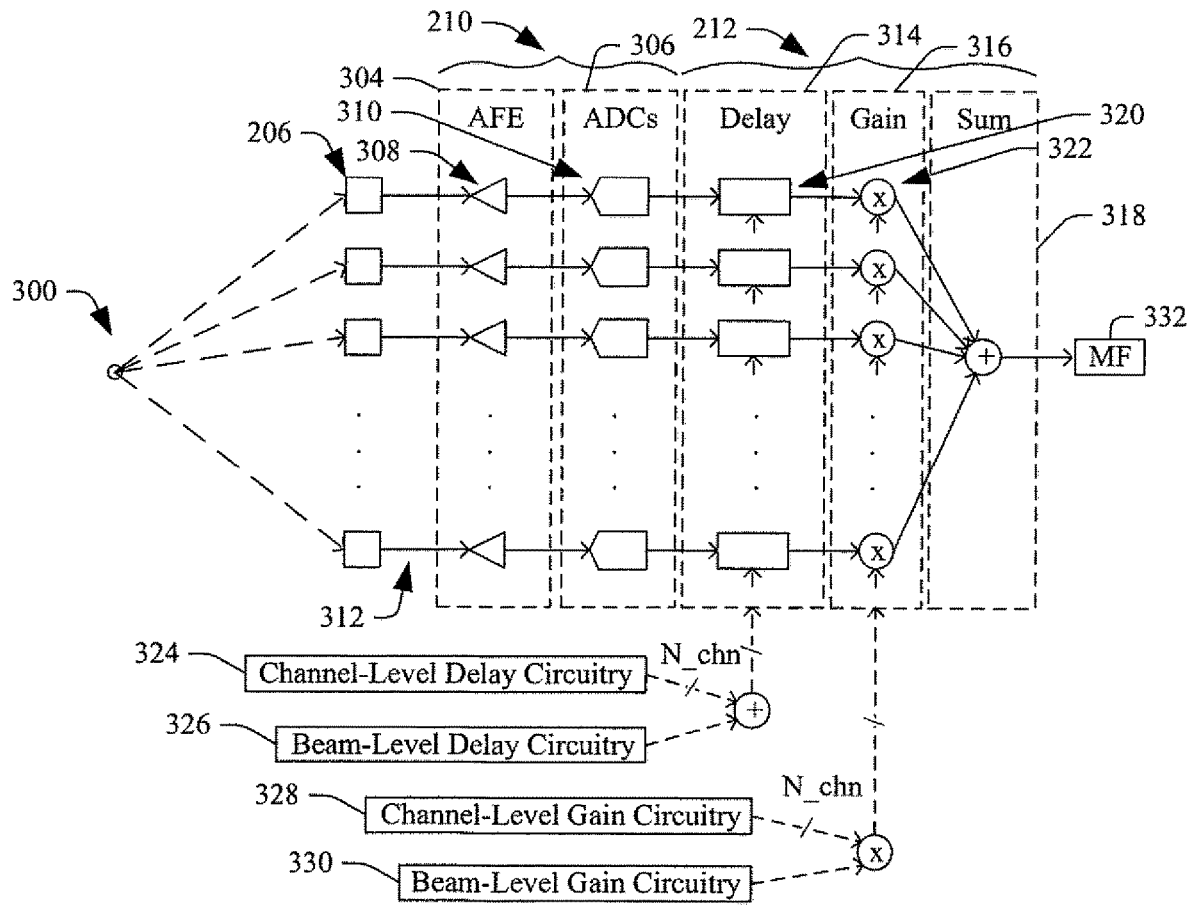
FIG. 3 schematically illustrates example receive circuitry and beamformer of the system of FIG. 2.

FIG. 3 illustrates an example of the elements 206, the receive circuitry 210 and the beamformer 212 in connection with an acoustical focal point 300 and echoes.

The receive circuitry 210 includes an analog front end (AFE) 304 and an analog to digital converter (ADC) 306. The AFE 304 includes an amplifier 308 and an ADC 310 for each channel 312. Each of the amplifiers 308 amplifies a corresponding analog electrical signal from a micro-volt level to a voltage range of ADC 306. In one instance, a gain of the channel 312 is set to amplify weak signals as high as possible without causing clipping of the signals. Each ADC 310 digitizes an amplified electrical signal.

The beamformer 212 includes delay circuitry 314, gain circuitry 316, and an adder/summer 318. The delay circuitry 314 includes a delay circuit 320 for each channel 312, and the gain circuitry 316 includes a gain circuit 322 for each channel 312. Channel-level delay circuitry 324 provides a channel-level delay value for each channel 312, and a beam-level delay circuitry 326 provides a beam-level delay value. Channel-level gain circuitry 328 provides a channel-level gain value for each channel 312, and a beam-level gain circuitry 330 provides a beam-level gain value.

The beamformer 212 can employ single or multi-stage beamforming. In single-stage beamforming (as illustrated in FIG. 3), the channel-level and beam-level delay is applied once and summed in only a single stage. In multi-stage beamforming such as dual-stage beamforming, the channel-level delay-and-sum is performed in a first stage, intermediate RF-beams are buffered, and the beam-level delay-and-sum is performed in a second-stage. In one instance, the delays can be applied with a precision of $1/16$ or better of the ultrasound wavelength ($\lambda$).

The values for the channel-level delays and the channel-level gain and the beam-level delays and the beam-level gain can be calculated using known and/or other approaches, e.g., based on the principles of STA focused flow imaging described in U.S. Pat. No. 7,542,790. The channel-level delays and gain and the beam-level delays and gain can be updated as a function of time providing full dynamic channel-level receive focusing and apodization versus scan depth and full dynamic beam-level receive focusing and apodization versus scan depth.

A matched filter (MF) 332, which is matched to an expected received echo-pulse shape (bandwidth), operates on each of the beamformer output beams. In a variation, the matched filter 332 can be a filter applied on each channel of the beam-former, or is omitted.

Figure 4:
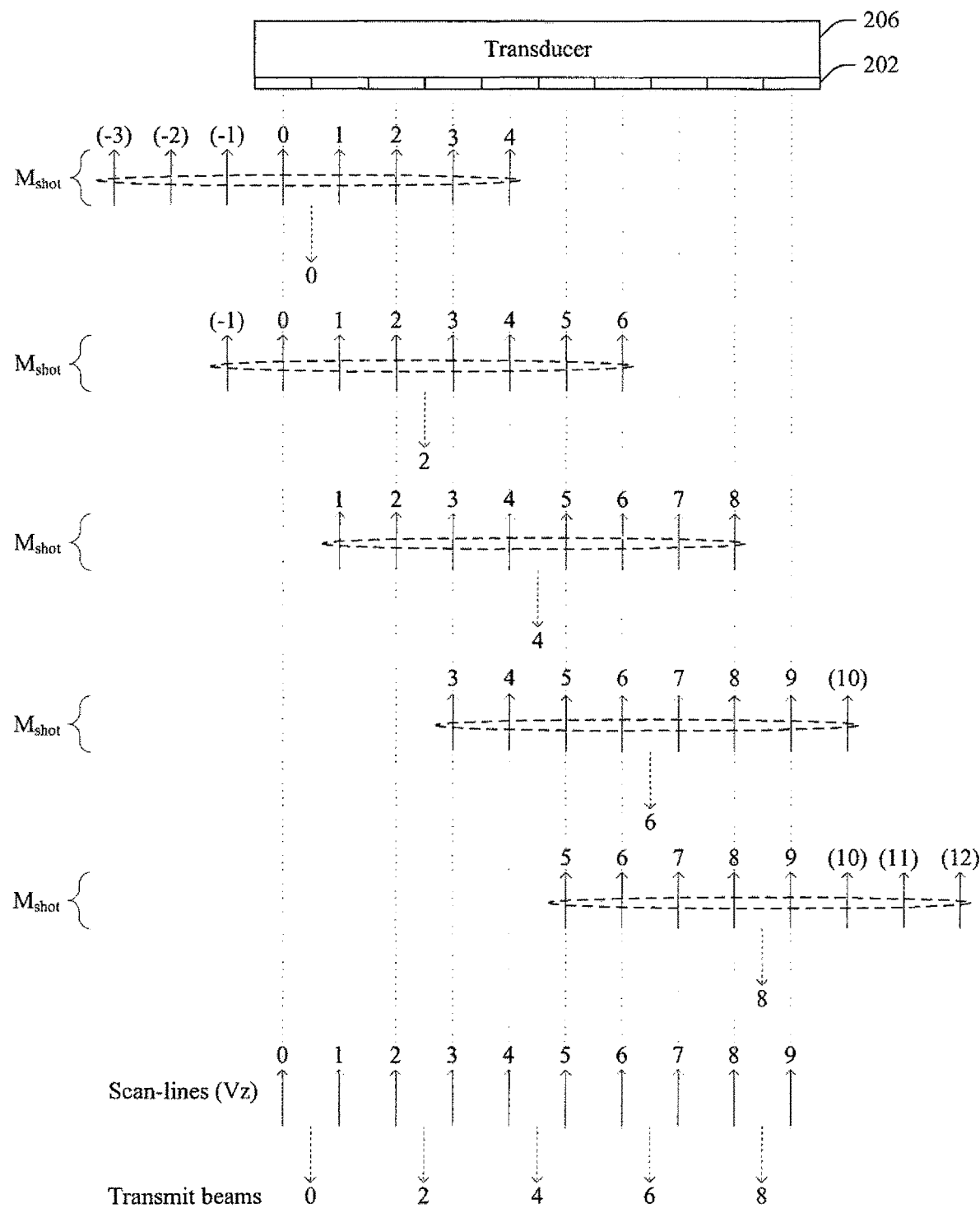
FIG. 4 schematically illustrates an acquisition sequence for the configuration of FIG. 2.

FIG. 4 illustrates an example of an acquisition-sequence for CFM imaging.

This acquisition-sequence is for a non-package-interleaved image of 10 scan lines per frame, 8 simultaneous receive-beams per acquisition-event, and 2 simultaneous velocity scan-lines per acquisition-package. Dashed arrows pointing away from the transducer array 202 illustrate transmit beams, and solid arrows pointing towards the transducer array 202 are receive beams. The first five rows show the acquisition event ($M_{shot}$) for each of the five receive-beam blocks from which the flow image is constructed. For each acquisition event, one beam is transmitted and a block of 8 beams is received. The bottom row shows the resulting location of the velocity scan-lines for the flow image and the location of the transmit beams from which they are beam-formed.

With a package-based approach, each acquisition event is repeated several times ($M_{shot} > 1$) to form an acquisition-package, from which movements can be estimated. With $M_{Shot}=2$, the sequence of acquisition events for a complete display frame is the transmit beams {0, 0, 2, 2, 4, 4, 6, 6, 8, 8}.

In the illustrated example, the effective C-Mode Pulse Repetition Frequency (PRFC) is equal to the maximum PRF and the velocity range is $V_{max}=0.5*L_z*PRFC$, where Lz is the axial wavelength Lz=C/F0, F0 is the center receive frequency and C is the speed of sound (e.g. 1540 m/s). The additional beams that extend beyond the edges of the image frame are discarded before display. As an example, an image of depth D=7 cm, $N_{Line}=192$ lines, 32 receive-beams, MultiLine=8 scan-lines per shot, $M_{Shot}=4$ and F0=5 MHz gives PRF=C/(2*D)=11.0 kHz, PRFC=PRF, a velocity range of V max=$0.5*L_z*PRFC$=169 cm/s and an acquisition frame-rate of FR=PRF/MShot/$N_{Line}$*MultiLine=115 Hz.

Another example acquisition sequence is sub-frame package-interleaved acquisition. The package-interleaved acquisition achieves a desired lower velocity range while maintaining the frame-rate. In FIG. 4, with $M_{shot}=2$ and a package-interleave factor of P=2, the sequence of acquisition events for two complete display frames is the transmit-beams {0, 2, 0, 2, 4, 6, 4, 6, 8, 0, 8, 0, 2, 4, 2, 4, 6, 8, 6, 8}. The effective C-mode pulse repetition frequency is PRFC=PRF/P and the velocity range is V max=$0.5*L_z*PRFC$=84.7 cm/s while the frame-rate is unchanged. In this example the acquisition-package consist of the acquired data for estimating P*2=4 velocity scan-lines for the flow image. This example also illustrates the possibility of acquisition-packages overlapping the image-frame boundary for optimal frame-rates if desired.

Another example is full-frame package-interleaved acquisition. This acquisition achieves a desired low velocity range while maintaining the frame-rate and achieving continuous data per receive-beam location. In FIG. 4, with $M_{shot}=1$ and a package-interleave factor of P=5, the sequence of acquisition events for one acquisition frame is the transmit-beams {0, 2, 4, 6, 8}. This sequence is repeated producing continuous data per receive-beam location at an effective C-mode pulse repetition frequency of PRFC=PRF/P. As an example, an image of depth D=7 cm, NLine=192 lines, 32 receive-beams, MultiLine=8 scan-lines per shot with F0=5 MHz gives package-interleave factor P=NLine/MultiLine=24, PRF=C/(2*D)=11.0 kHz, PRFC=PRF/P=458 Hz, a velocity range of V max=$0.5*L_z*PRFC$=7.1 cm/s and an acquisition frame-rate of FR=PRF/MShot/NLine*MultiLine=PRFC=458 Hz.

Returning to FIG. 2, preprocessing circuitry 214 preprocesses the beamformed RF data. For velocity estimation, this includes transforming the beam-data from the RF-data domain to the complex-value I/Q-data domain, e.g., with a Hilbert Transform Filter, by the combination of a Complex-Demodulation, Band Pass Filter and optional Decimation for data reduction, and/or otherwise. The signal processing can be combined with high dynamic range (HDR) color flow imaging. An example of HDR color flow imaging is described in application Ser. No. 14/801,653 to Haugaard et al., filed Jul. 28, 2015, and entitled "High Dynamic Range Ultrasound Flow Imaging," the entirety of which is incorporated herein by reference.

The console 204 further includes a velocity processor 216. Data for package-based velocity estimation are acquired as beam-data that are sampled at a Sample Frequency (FS) of e.g. 15-60 MHz versus time (scan-line depth). The time-dimension defined by FS is referred to herein as FS-time dimension. A number ($M_{shot}$) of ultrasound pulses are transmitted (shot) to receive back beam-data that are acquired in the same beam-direction versus time at a Pulse Repetition Frequency (PRF) of 200 Hz-20 kHz and collected into an acquisition-package. The time domain defined by the PRF is referred to herein as PRF-time dimension.

The velocity processor 216, in a first stage, high-pass filters (e.g., with a Wall filter (WF)) along the PRF-time dimension of each receive-beam to remove high-amplitude stationary signals and high-amplitude signals from slow moving objects like the walls of the blood vessels. The WF can be a FIR-based, IIR-based, or arbitrary matrix filter. In case of full-frame package-interleaved acquisition with continuous data per receive-beam location, the Wall Filter might be a direct IIR filter that realizes a HPF with very narrow transition-band for optimal flow sensitivity in the Doppler frequency-band (velocity-range) of interest. The velocity processor 216, in a second stage, estimates an autocorrelation (AC) along the PRF-time dimension of each receive-beam.

The velocity processor 216, in a third stage, applies an averaging filter on the output. The averaging may be done in the FS-time dimension, over several acquisition packages, in the lateral beam dimension, and/or in the temporal frame dimension in order to improve the blood-flow sensitivity or resolution further. The acquisition-packages might consist of data from fully overlapping transmit/receive beam-directions or partially overlapping transmit/receive beam directions. For high resolution STA compound color flow imaging, this stage adds the overlapping AC outputs from acquisition-packages of overlapping transmit/receive beam-directions. The complex-value I/Q-data AC outputs are added as-is, i.e. as they are formed by the STA beamforming.

The velocity processor 216, in a fourth stage, estimates phase, e.g., by calculating an arctangent operation on the summed AC output and/or otherwise. In the illustrated embodiment, the velocity processor 216, in a fifth stage, applies an average filter on the velocity (phase) estimates. The averaging may be done in the FS-time dimension, in the lateral scan-line direction, and/or in the temporal frame dimension in order to improve the blood-flow sensitivity further. In a variation, the velocity processor 216 does not apply the average filter; i.e., the averaging is omitted.

Figure 5:
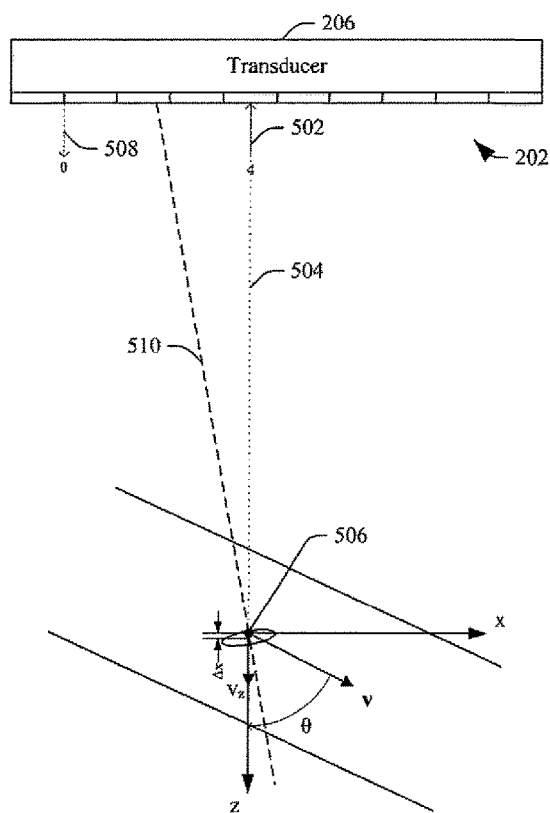
FIG. 5 schematically illustrates an example of a tilted and translated ultrasound field point spread function within a blood vessel for a channel-only beam-formed receive-beam furthest away from the transmit-beam.

An example of how the adding of the overlapping AC outputs in the third stage turns the acquired receive beams into high resolution STA compound images without beamforming artifacts is described next in connection with FIG. 5, which illustrates the geometry of the acquisition-event of transmit-beam 0 and receive-beam 4 from FIG. 4. In FIG. 5, a receive-beam 502 is located in a center of a given scan-line 504 direction (the finely dashed line). Moving through the beam 502 is an object 506 with velocity-vector v. The velocity that is measured in CFM is the axial component $v_z$. However, since a transmit-beam 508 has a slightly different direction, a resulting pulse-echo beam direction (the dashed line) 510 is orientated between the transmit-beam 508 and the receive-beam 502, and an acoustical pulse-echo ultrasound point spread function (PSF) is tilted in that direction.

Figure 6:
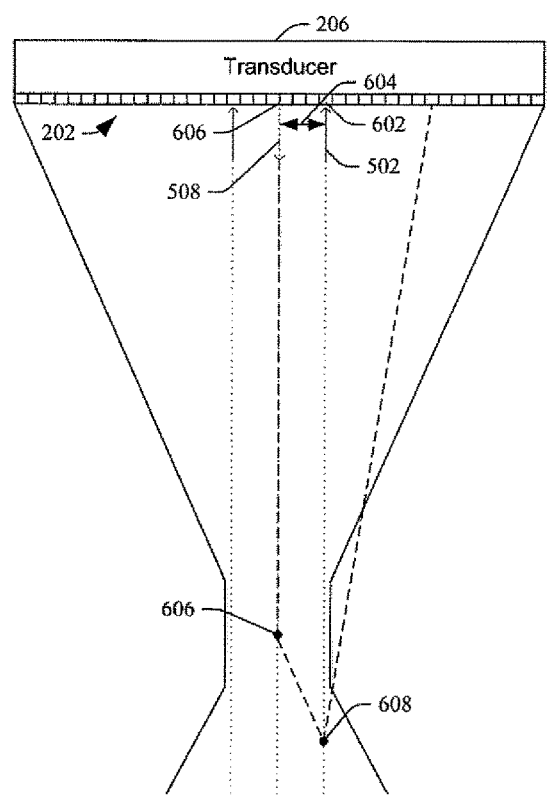
FIG. 6 schematically illustrates an example of estimated depth-dependent width of the transmit-beam relative to the transmit-focus point.
Figure 7:
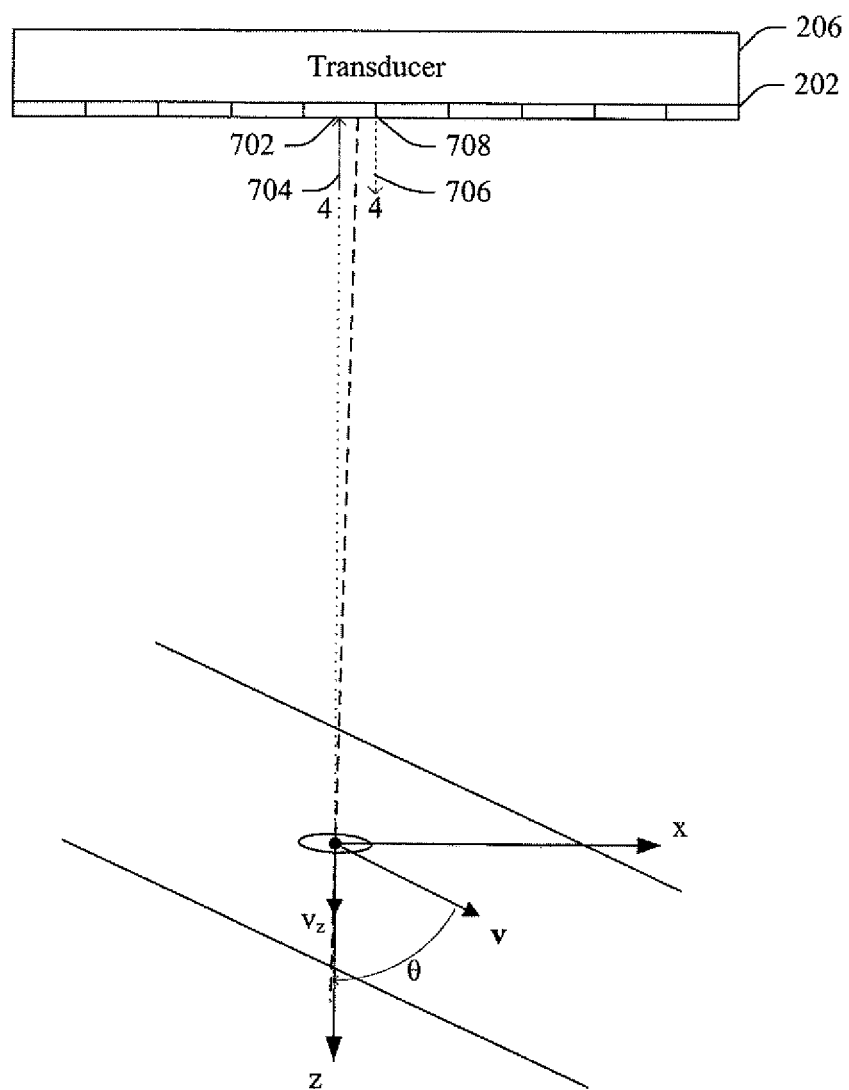
FIG. 7 schematically illustrates an example of a tilted ultrasound field point spread function within a blood vessel for a channel-only beam-formed receive-beam close to the transmit-beam.

With a focused transmit-beam 508, as illustrated in FIG. 6, an origin 602 of the receive-beam 502 is located a finite distance 604 away from an origin 602 of the transmit-beam 508, and a time-of-flight distance from the transmit origin 602 to a transmit-focus point 606 and from the transmit-focus point 606 to a receive-focus point 608 on the receive-beam 502 is extended, resulting in a depth-dependent translation ($\Delta x$) (FIG. 5) of the point spread function. For comparison, FIG. 7 illustrates the geometry of the acquisition-event of transmit-beam 4 and receive-beam 4 from FIG. 4. In this instance, an origin 702 of a receive-beam 704 (receive-beam 4) from a transmit-event of a transmit beam 706 (transmit-beam 4) is close to an origin 708 of the transmit-beam 706 and a transmit-focus point, and the translation $\Delta x$ of the PSF is very small, relative to that shown in FIG. 5.

Returning to FIG. 4, the shape and position of the PSF of each receive-beam is chosen such that if the four receive-beam 4 from acquisition-events with transmit-beam 0, 2, 4 and 6 where added, the resulting PSF would have zero tilt and, preferably but not necessarily, be symmetric. This may ensure that the summed AC outputs of the four receive-beam 4 into scan-line 4 has zero tilt and have the same amplitude sensitivity as the sum of four receive-beams for any other scan-line, except for at the edges of the image. A pair-wise asymmetry of the summed PSF may be without visible artifacts in the flow image as long as the tilt is zero and the energy it contains is constant. This allows for a larger selection of acquisition sequences to choose from for frame-rate optimization.

The shape of the PSF is determined by the STA beamforming. The beam-level delay circuitry 326 calculates the dynamic beam-level delay for the STA beamforming such that the beamforming realigns all the receive-beam PSFs before the AC outputs are added in the third stage of the velocity estimator. The weight by which each receive-beam shall contribute to the STA beamforming depends on the depth-dependent pulse-echo ultrasound field. The beam-level gain circuitry 330 calculates the dynamic beam-level gain (apodization) of the STA beamforming according to an estimated depth-dependent width of the transmit-beam as illustrated in FIG. 6.

In one instance, the velocity processor 216 is configured to determine velocity blood flow from the formed receive-beams by wall filtering each receive-beam, determining the auto-correlation of each receive-beam, adding the auto-correlation of receive-beams from different acquisition-packages and determining the phase of the summed auto-correlations. Additionally or alternatively, the velocity processor 216 is further configured to determine an amplitude/power of the summed auto-correlations for use in tissue discrimination.

Additionally or alternatively, the velocity processor 216 is further configured to discriminate between tissue and flow by determining the amplitude/power of each receive-beams before/after wall filtering, adding the amplitude/power of receive-beams from different acquisition-packages, estimates average threshold values from the summed amplitude/power information and makes threshold-processing on the high-resolution velocity information. More particularly, the velocity processor 216 can include a tissue discriminator configured to detect whether estimated movement information is originating from blood flow, from tissue, or is background noise. In one instance, detection of movement from tissue and detection of background-noise is done by comparing the amplitude of the signal against a single or depth-dependent average threshold-value.

Speckle-noise is an inherent artifact in ultrasound imaging, which is produced by spatially inhomogeneous tissue that causes a mosaic of constructive/destructive interference pattern in the received signal. This can be a significant issue in conventional flow imaging approaches, as destructive interference (drops in the signal amplitude) makes threshold-processing of a high-resolution signal very hard. The resulting speckle-noise pattern in the receive signal is dependent on the location/direction at which the tissue was insonified. Speckle-noise in an amplitude- or power-signal receive-beam can be reduced by forming a new receive-beam that is the average (compounding) of several STA beam-formed receive-beams acquired with different locations/directions of the transmit-beam.

Since the AC output above is a complex-value I/Q power-signal and the summed AC output is formed from a sum of receive-beams from acquisition-events with different location/direction of the transmit-beam, the summed AC output is speckle-noise reduced. This has a significant impact on the tissue discrimination as it makes threshold-processing of a high-resolution signal easier producing flow images almost without speckle-noise artifacts (black holes). In addition, the average threshold-values used, which might be estimated from the amplitude/power of the unfiltered input signal, can be significantly improved as well by forming the amplitude/power signal as the sum of the amplitude/power of the unfiltered input-signal receive-beams.

With respect to FIG. 2, the console 204 further includes a power processor 218. The power processor 218 is based on a dedicated power estimator of the input acquisition-packages, the output of the AC above and/or otherwise. Following stages one to three above, the fourth stage for the power estimator is to derive the absolute value (Pythagoras operation) of the summed output of the AC. The output of the power estimator is mapped to the desired e.g. 8-bit display precision. This can be done by a logarithmic (log)-based Dynamic Range Compression (DRC) with control parameter range for the input dynamic range setting and gain for an overall gain setting. A fifth stage before delivering data for display, is an optional Averaging Filter on the power estimates. The averaging may be done in the FS-time dimension, in the lateral scan-line direction, and/or in the temporal frame dimension in order to improve the blood-flow sensitivity further.

The console 204 further includes a variance processor 220. The variance processor 220 can be based on a dedicated variance estimation of the input acquisition-package or based on the output from the first stage (WF) and the summed AC output of the third stage of velocity estimator above. The second stage of the variance processor 220 is a second amplitude/power estimator that estimates the signal power along the PRF-time dimension of each receive-beam.

The third stage of variance processor 220 is an averaging filter on the output of the second amplitude/power estimator. The averaging may be done in the FS-time dimension, over several acquisition packages, in the lateral beam dimension, and/or in the temporal frame dimension in order to improve the blood-flow sensitivity or resolution further. The acquisition packages might consist of data from fully overlapping transmit/receive beam-directions or partially overlapping transmit/receive beam direction. For high resolution STA compound color flow imaging, this stage adds the overlapping amplitude/power outputs from acquisition-packages of overlapping transmit/receive-beam directions. The real-value amplitude/power outputs must be added as-is, i.e. as they are formed by the STA beam-forming.

At the fourth stage of the variance processor 220, the variance is derived from the summed AC output and the summed output of a second amplitude/power estimator, and the result is an e.g. 8-bit unsigned output. A fifth stage before delivering data for display, is an optional averaging filter on the variance estimates. The averaging may be done in the FS-time dimension, in the lateral scan-line direction, and/or in the temporal frame dimension in order to improve the blood-flow sensitivity further.

The console 204 further includes an image processor 222. The image processor 222 processes the data from the preprocessing circuitry 214 and generates an image such as a B-mode and/or other image.

The console 204 further includes a rendering engine 224 and a display 226. The rendering engine 224 visually presents, via the display 226, the image generated by the image processor 222 with flow information generated by the velocity processor 216 superimposed there over. Optionally, power information generated by the power processor 218 and/or variance information generated by the variance processor 220 can be visually presented. Indicia such as color, arrows, etc. can be used to show magnitude and/or direction.

The console 204 further includes a user interface (UI) 228 with one or more input devices (e.g., a button, a knob, a slider, a touch pad, a mouse, a trackball, a touch screen, etc.) and/or one or more output devices (e.g., a display screen, a light, an audio generator, etc.), which allow for interaction between a user and the ultrasound imaging system 200. The console 204 further includes a controller 230 configured to control one or more of the components of the console 204, the transducer array 202, and/or other device.

In one instance, one or more of the components (e.g., 216, 218, 220 and/or 222) of the console 204 can be implemented via one or more processors (CPU, microprocessor, controller, etc.) executing one or more computer readable instructions encoded or embedded on computer readable storage medium, which is a non-transitory medium such as physical memory or other non-transitory medium, and excludes transitory medium. Additionally or alternatively, at least one of the instructions can be carried by a carrier wave, a signal, or other transitory medium.

The ultrasound imaging system 200 can be part of a portable system on a stand with wheels, a system residing on a tabletop, and/or other system in which the transducer array 202 is housed in a probe or the like, and the console 204 is housed in an apparatus separate therefrom. In another instance, the transducer array 202 and the console 204 can be housed in a same apparatus such as within a single enclosure hand-held ultrasound scanning device.

Variations are contemplated next.

Figure 8:
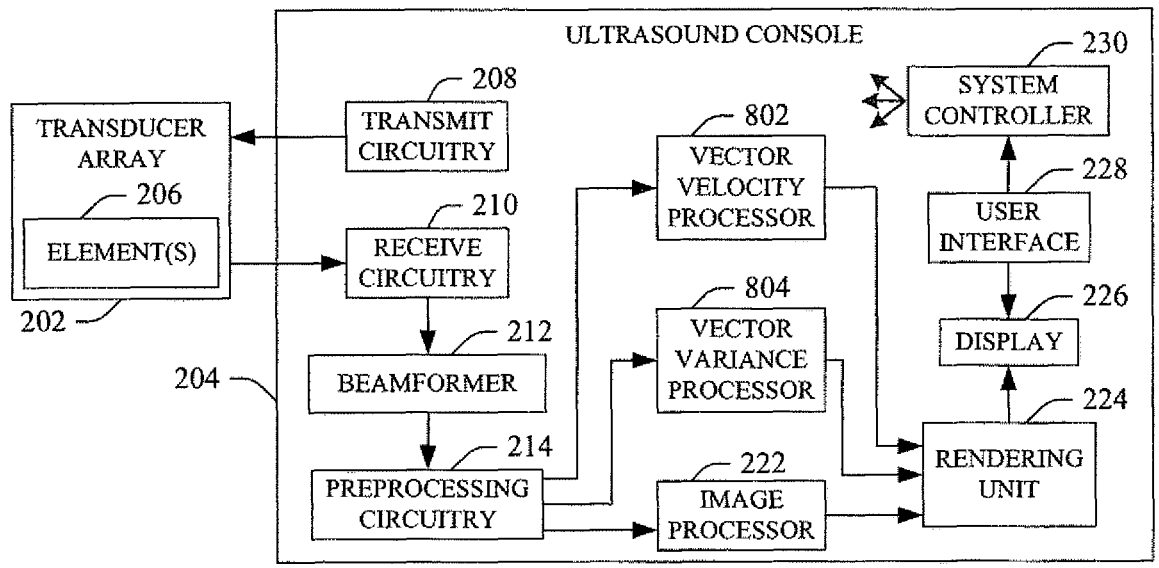
FIG. 8 schematically illustrates an example ultrasound imaging system configured for vector flow imaging.

FIG. 8 schematically illustrates a variation of ultrasound imaging system 200 of FIG. 2 configured for STA vector flow imaging.

In one variation, the STA focusing beamformer 212 includes 8×3 to N×3 (where N is 64 or more) parallel beams. For instance, vector flow imaging based on the Transverse Oscillation (TO) method uses three (3) times as many receive-beams per acquisition-event. The first receive-beam is located on the center of the scan-line direction and the two other beams are located at a distance of +/−⅛ of a lateral wavelength relative to the first beam. The acquisition-sequence for vector-velocity flow imaging is as shown in FIG. 4 except that each receive beam is now split-up into receive-beam-groups of 3 receive-beams.

In another variation, the STA focusing beam-former beamformer 212 beamforms with lateral-decimation. CFM and VFI systems operate in general at a lower axial and lateral resolution than B-mode imaging (e.g. one scan-line per transducer-element) in order to achieve the desired flow sensitivity and display frame-rate. The estimation of the lateral-velocity component based on a TO-method uses a lateral wave-length of typically four (4) times the transducer element-pitch. This is discussed in U.S. Pat. No. 6,859,659 B1, filed May 10, 2000, and entitled "Estimation of vector velocity," the entirety of which is incorporated herein by reference.

Since the spatial resolution is related to the wave-length of the interrogating ultrasound field, the lateral resolution of the lateral-velocity component is approximately four (4) times the element-pitch. Hence, according to Nyquist sampling theorem, the lateral-velocity estimation can ideally be sampled at half this distance (two (2) times the pitch), which in this example is one scan-line at every second transducer-element. This approach can be used to reduce the number of required receive-beams without severe lateral spatial aliasing and visible artifacts in the displayed flow image. Prior to display of the vector-velocity information, the decimated scan-lines with the lateral-velocity component are interpolated by a factor of two (2) and aligned by the display unit to match the number of scan-lines with the axial-velocity component.

Figure 9:
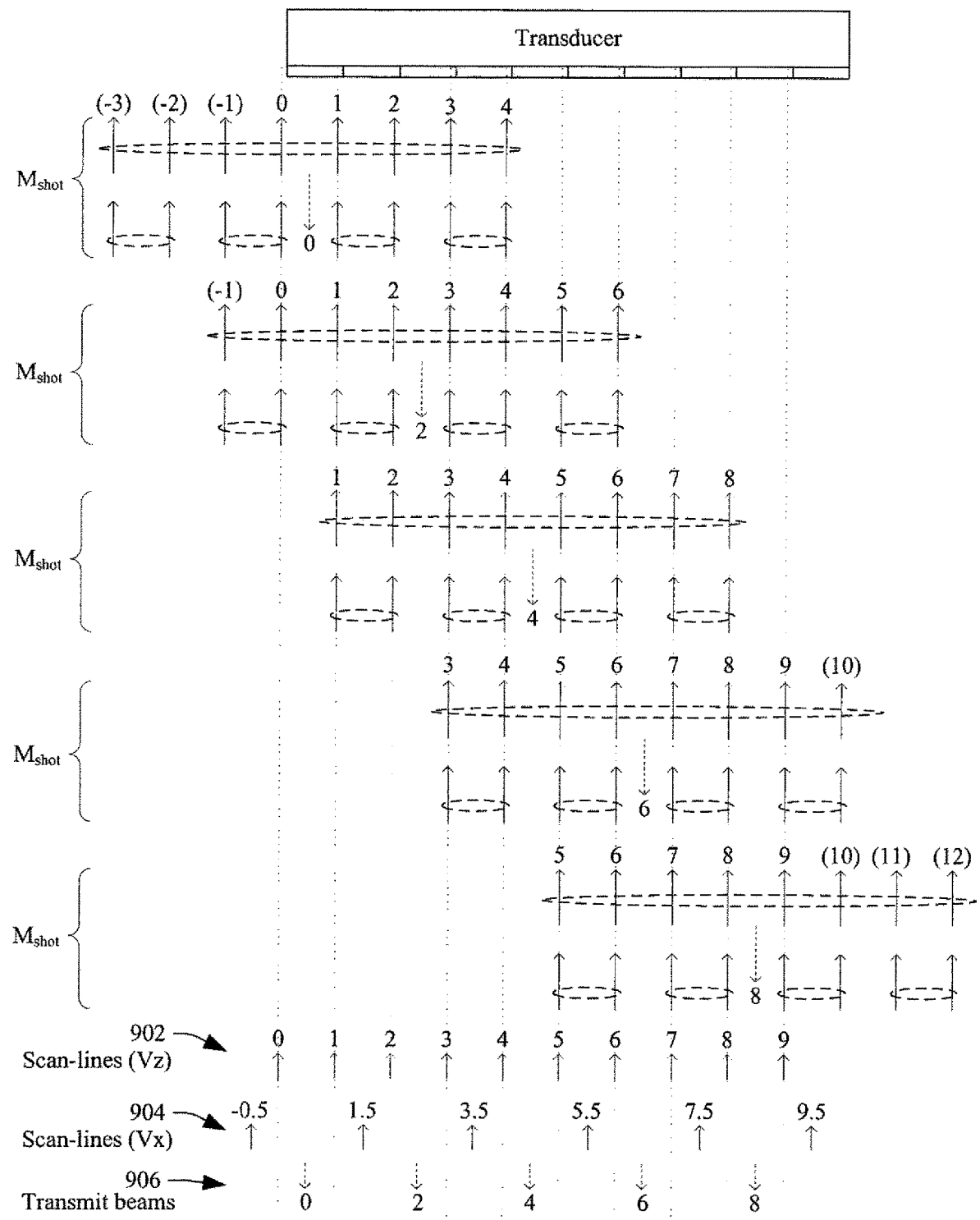
FIG. 9 schematically illustrates an acquisition sequence for the configuration of FIG. 8.

An example of an acquisition-sequence for vector-velocity flow imaging with lateral decimation is illustrated in FIG. 9. In FIG. 9, each receive beam of FIG. 4 is split-up into receive-beam-groups of three (3) receive-beams and then the receive-beam-pairs for estimation of the lateral component is decimated by 2, resulting in a total number of receive-beams of this example of NB=8*2=16 receive-beams per acquisition-event. The four receive-beam-pairs for estimation of the lateral component are located to achieve best symmetry relative to the transmit beams. In this example, they align with the 8 receive-beams for estimating the axial component.

The bottom three rows illustrated a resulting spatial location of axial-velocity ($V_z$) scan-lines 902, lateral-velocity ($V_x$) scan-lines 904 and the original location of the transmit-beams 906. The spatial location of the lateral-velocity scan-lines is fractional compared to the axial-velocity scan-lines. Prior to display of the vector-velocity information, the decimated scan-lines with the lateral-velocity component are interpolated by a factor of 2 and aligned by the display unit to match the number of scan-lines with the axial-velocity component, forming the missing lateral-velocity scan-line.

Returning to FIG. 8, the console 204 includes a vector-velocity processor 802 and a vector-variance processor 804.

The vector-velocity processor 802, in a first stage, high-pass filters (e.g., with a Wall filter (WF) and/or other filter) along the PRF-time dimension of each receive-beam-group of three (3) receive-beams to remove high-amplitude stationary signals and high-amplitude signals from slow moving objects like the walls of the blood vessels. A suitable WF includes a mean-subtraction filter, a FIR-based, IIR-based, an arbitrary matrix filter, and/or other WF. The vector-velocity processor 802, in a second stage, estimates single- and double autocorrelations (ACs) along the PRF-time dimension of each receive-beam-group, resulting in an axial and lateral component.

The vector-velocity processor 802, in a third stage, applies an averaging filter, one on each on the two AC output components. The averaging may be done in the FS-time dimension, over several acquisition packages, in the lateral beam dimension, and/or in the temporal frame dimension in order to improve the blood-flow sensitivity or resolution further. The acquisition packages might consist of data from fully overlapping transmit/receive-beam directions or partially overlapping transmit/receive-beam direction. For high resolution STA compound vector-velocity flow imaging, this stage adds the overlapping AC outputs from acquisition packages of overlapping transmit/receive-beam directions. The complex-value I/Q-data AC outputs must be added as-is, i.e. as they are formed by the STA beam-forming.

The vector-velocity processor 802, in a fourth stage, estimates phase, e.g., by calculating two arctangent operations, one on each of the summed AC output components. The vector-velocity processor 802, in a fifth stage, applies an averaging filter on the velocity (phase) estimates. The averaging may be done in the FS-time dimension, in the lateral scan-line direction, and/or in the temporal frame dimension in order to improve the blood-flow sensitivity further. This is done for each of the two vector-velocity components. In a variation, the fifth stage is omitted.

The vector-variance processor 804 can be based on a dedicated variance estimation of the input acquisition data package, the output from the first stage (WF) and the summed AC output of the third stage of vector-velocity estimation, and/or otherwise. A second stage of the vector-variance processor 804 includes a double amplitude/power estimator that estimates the axial and lateral power-signal components along the PRF-time dimension of each receive-beam-group.

A third stage of the vector-variance processor 804 applies a double averaging filter, one on each of the output components of the amplitude/power estimator. The averaging may be done in the FS-time dimension, over several acquisition packages, in the lateral beam dimension, and/or in the temporal frame dimension in order to improve the blood-flow sensitivity or resolution further. The acquisition packages might consist of data from fully overlapping transmit/receive-beam directions or partially overlapping transmit/receive-beam directions. For high resolution STA compound vector-variance flow imaging, this stage adds the overlapping amplitude/power outputs from acquisition-packages of overlapping transmit/receive-beam directions. The real-value amplitude/power outputs are added as-is, i.e. as they are formed by the STA beam-forming.

A fourth stage of the vector-variance processor 804 derives a vector-variance from the axial and lateral summed AC outputs and the axial and lateral summed outputs of the double amplitude/power estimator as e.g. an 2×8-bit unsigned output. A fifth stage of the vector-variance processor 804 applies an averaging filter on the vector-variance estimates. The averaging may be done in the FS-time dimension, in the lateral scan-line direction, and/or in the temporal frame dimension in order to improve the blood-flow sensitivity further. This is done for each of the two vector-variance components. In a variation, the fifth stage is omitted.

Figure 10:
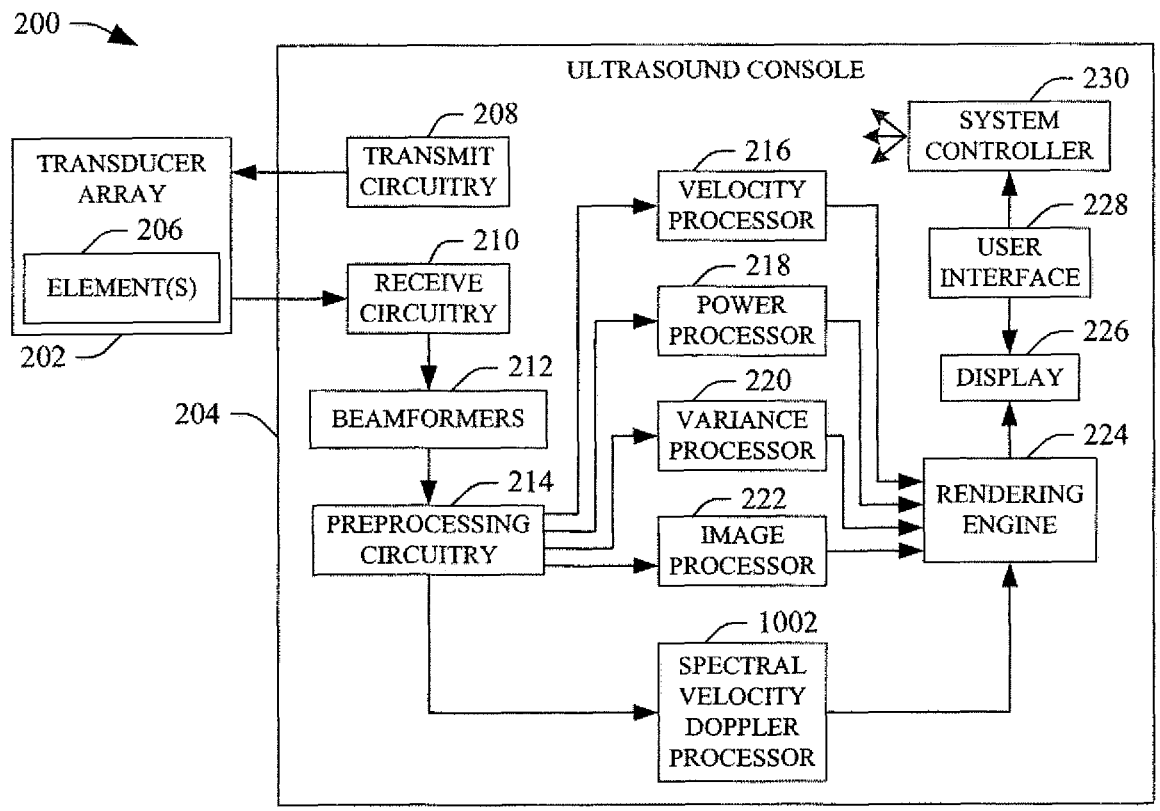
FIG. 10 schematically illustrates a variation of FIG. 2 further configured for spectral velocity Doppler imaging.

FIG. 10 schematically illustrates a variation of ultrasound imaging system 200 of FIG. 2 configured for spectral velocity Doppler imaging and includes a spectral velocity Doppler processor 1002.

Ultrasound spectral velocity pulsed-wave Doppler (PWD) is a 1D time-motion mode, where the acquisition is conventionally performed along a single scan-line through a blood vessel. The range of acquired data is from where the scan-line overlaps the blood vessel is extracted (Range-Gated). From a number of acquisition-event an acquisition-package is collected, the velocity distribution is calculated and displayed as e.g. a Doppler-frequency/velocity spectrogram-image with time along the horizontal x-axis and velocity along the y-axis and the intensity of each pixel indicating the amplitude/power spectral density (PSD) function of the flow.

The spectral velocity Doppler processor 1002, before the estimation of the velocity PSD, the acquisition-package is Wall-Filtered along the PRF-dimension. The velocity PSD line can be estimated using e.g. an FFT-based method like the Welch method or other. Alternatively or in addition, the flow information might be displayed as curves with minimum velocity, mean velocity, maximum velocity, variance or standard-deviation curves or other statistics.

An example of an acquisition sequence for STA compound spectral velocity Doppler can be deduced from FIG. 4. Assuming that the scan-line 4 is the direction of interest, the acquisition sequence would be to repeat acquisition-event with transmit-beam 4. This acquisition-sequence is repeated to acquire an acquisition-package from which the PSD line can be calculated. The PSD line is calculated for each of the range-gated and wall-filtered receive-beams from e.g. 1 to 8 and added to form the one final velocity PSD line for scan-line 4 to display. The final summed velocity PSD line will have improve signal-to-noise and reduced speckle-noise like the summed autocorrelation of the color velocity estimator above, and represent a laterally multi-gated sampling. In this example, the Doppler PRF is PRFD=PRF and new data for the velocity PSD estimations in obtained for each acquisition-event.

Another example of an acquisition sequence for STA compound spectral velocity Doppler can also be deduced from FIG. 4. Assuming that the scan-line 4 is the direction of interest, the acquisition sequence would be acquisition-events of transmit-beam 0, 2, 4 and 6. This acquisition sequence is repeated to acquire an acquisition-package from which the velocity PSD line can be calculated. The velocity PSD line is calculated for each of the range-gated and wall-filtered receive-beams 4 and added to form the one final velocity PSD line for scan-line 4 to display. The final summed velocity PSD line will have improve signal-to-noise and reduced speckle-noise like the summed autocorrelation of the color velocity estimator above.

Note that only receive-beams 4 from each acquisition-event are actually used here and hence needs to be beam-formed or data from receive-beams 3 and 4 can be used to add laterally-positioned samples to the velocity PSD estimation. In this example the effective Doppler PRF is PRFD=PRF/P, where P is the interleave-factor of the acquisition-package, here P=4. To obtain new data for the velocity PSD estimation in each acquisition-event, one can use a recursive summing of the velocity PSD line of each receive-beam, where the oldest PSD line is subtracted and the newest is added to previous summed velocity PSD line.

Figure 11:
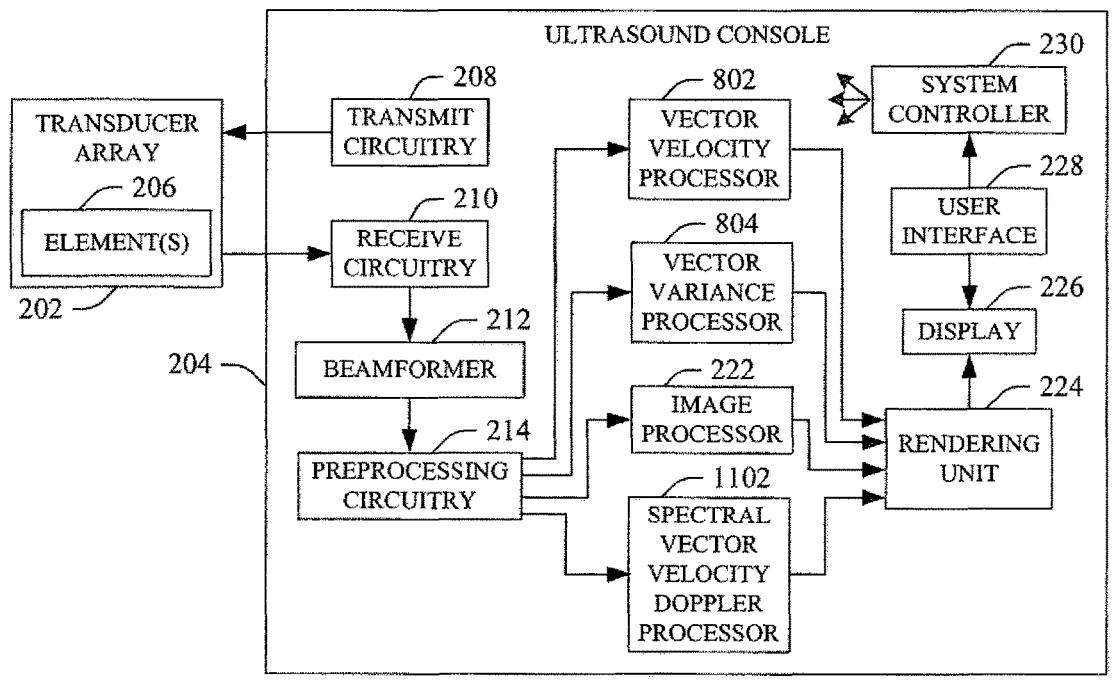
FIG. 11 schematically illustrates a variation of FIG. 8 further configured for spectral vector velocity Doppler imaging.

FIG. 11 schematically illustrates a variation of ultrasound imaging system 200 of FIG. 2 configured for spectral vector velocity Doppler imaging and includes a spectral vector velocity Doppler processor 1102.

Ultrasound Spectral Vector-Velocity Pulsed-Wave Doppler is a 1D time-motion mode, where the acquisition is performed along a single scan-line through a blood vessel. The range of acquired data is from where the scan-line overlaps the blood vessel is extracted (Range-Gated). Assuming Transverse Oscillation (TO)-based vector-velocity, from a number of acquisition-event two acquisition-packages are collected, the vector-velocity distribution is calculated and displayed as e.g. a vector-velocity spectrogram-image with time along the horizontal x-axis and velocity along the y-axis and the color-coding of each pixel indicates the amplitude/power spectral density (PSD) function and the direction of the flow using color-coding.

The spectral vector velocity Doppler processor 1102, before estimating the velocity PSD, the acquisition-packages is Wall-Filtered along the PRF-dimension of each receive-beam-group of 3 receive-beams. The vector-velocity PSD line can be estimated using e.g. an FFT-based method like the Welch method or other. Alternatively, the spectrogram might show absolute-velocity power-level along a given flow direction or use other display methods. Furthermore, or in addition, the flow information might be displayed as curves with minimum velocity, mean velocity, maximum velocity, variance or standard-deviation curves or other statistics.

An example of an acquisition sequence for STA Compound Spectral Vector-Velocity Doppler can be deduced from FIG. 4. Assuming that the scan-line 4 is the direction of interest, the acquisition sequence would be to repeat the acquisition-event with transmit-beam 4. This acquisition-sequence is repeated to acquire two acquisition-packages from which the vector-velocity PSD line can be calculated. The vector-velocity PSD line is calculated for each of the range-gated and wall-filtered receive-beam-groups from e.g. 1 to 8 and added to form the final PSD line for scan-line 4 to display. The final summed vector-velocity PSD line will have improved signal-to-noise and reduced speckle-noise like the summed auto-correlation of the color velocity estimator above, and represent a laterally multi-gated sampling. In this example, the Doppler PRF is PRFD=PRF and new data for the velocity PSD estimations in obtained each acquisition-event.

Another example of an acquisition sequence for STA Compound Spectral Vector-Velocity Doppler can also be deduced from FIG. 4. Assuming that the scan-line 4 is the direction of interest, the acquisition sequence would be acquisition-events of transmit-beam 0, 2, 4 and 6. This acquisition sequence is repeated to acquire two acquisition-packages from which the vector-velocity PSD line can be calculated. The vector-velocity PSD line is calculated for each of the range-gated and wall-filtered receive-beams 4 and added to form the one final vector-velocity PSD line for scan-line 4 to display. The final summed vector-velocity PSD line will have improved signal-to-noise and reduced speckle-noise like the summed auto-correlation of the color velocity estimator above.

Note that only receive-beams 4 from each acquisition-event are actually used here and hence needs to be beamformed or data from receive-beams 3 and 4 can be used to add laterally-positioned samples to the vector-velocity PSD estimation. In this example the effective Doppler PRF is PRFD=PRF/P, where P is the interleave-factor of the acquisition-package, here P=4. To obtain new data for the vector-velocity PSD estimation in each acquisition-event, recursive summing of the vector-velocity PSD line of each receive-beam-group can be used, where the oldest vector-velocity PSD line is subtracted and the newest is added to previous summed vector-velocity PSD line.

It is to be appreciated that one or more of the examples (e.g., FIGS. 2, 8, 10 and and/or 11) described herein can be combined and/or modified.

Figure 12:
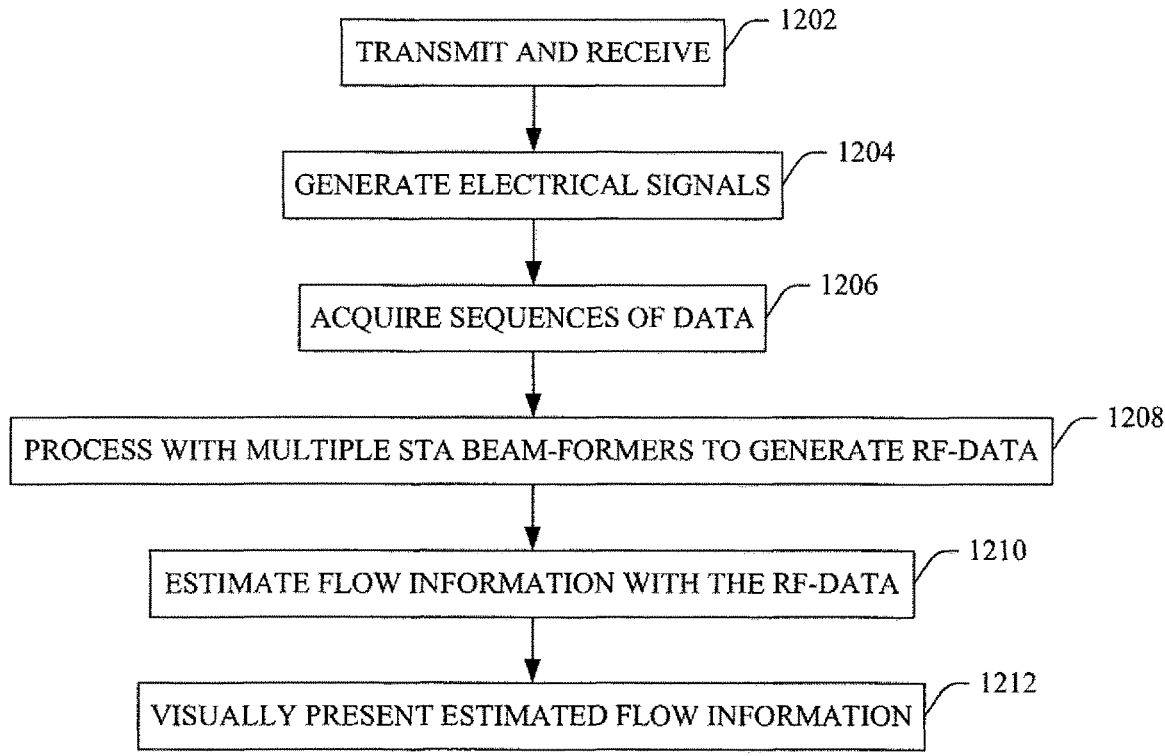
FIG. 12 illustrates an example method in accordance with an embodiment herein.

FIG. 12 illustrates an example method.

It is to be understood that the following acts are provided for explanatory purposes and are not limiting. As such, one or more of the acts may be omitted, one or more acts may be added, one or more acts may occur in a different order (including simultaneously with another act), etc.

At 1202, a transducer array transmits an ultrasound signal and receives a set of echo signals generated in response to the ultrasound signal interacting with moving structure.

At 1204, the transducer array generates electrical signals indicative of the received set of echo signals.

At 1206, receive circuitry acquires sequences of data, as described herein and/or otherwise.

At 1208, the sequences of data are processed with multiple STA beam-formers to generate beams of RF-data, as described herein and/or otherwise.

At 1210, flow information is estimated from the beams of RF-data, as described herein and/or otherwise.

At 1212, the flow information is visually presented. The flow information can be visually presented with or without an ultrasound image, which is generated with the electrical signals.

Aspects of an embodiment described herein include one or more block-based processing where only data for a subset of an image is stored instead of storing full sized data sets for whole image, scalable axial-resolution versus processing-bandwidth requirements by processing on base-banded and optionally decimated I/Q-data, option for use of conventionally focused transmit beams, use of robust auto-correlation-based velocity-estimator, use of cross-correlation-based velocity-estimator, parallel data acquisition, velocity bias and standard-deviation comparable or better than conventional CFM imaging methods using focused transmit-beams, velocity bias and standard-deviation improves (inverse-proportional) with the number of shots per scan-line direction and the number of summed receive-beams, etc.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound system, comprising:
 a transducer array with a plurality of transducer elements configured to transmit a pulsed field beam into a scan field of view, receive echo signals produced in response to the pulsed field interacting with particles/structure flowing/moving in the scan field of view, and generate electrical signals indicative of the echo signals;
 a beamformer including multiple synthetic transmit aperture beamformers configured to process the electrical signals over a plurality of processing channels into corresponding receive-beams of RF-data with a beam-level delay, channel-level delays, a beam-level gain and channel-level gains;

a velocity processor configured to estimate a velocity of the particles/structure flowing/moving in the scan field of view from the RF-data; and a rendering engine configured to display the flow velocity estimate on a display with color-coding.

2. The system of claim 1, wherein the velocity processor estimates the flow velocity by wall filtering each receive-beam, determining an auto-correlation of each receive-beam, adding the auto-correlation of receive-beams from different acquisition-packages to produce summed auto-correlations, and determining a phase of the summed auto-correlations.

3. The system of claim 2, wherein the velocity processor further discriminates between tissue and flow by determining an amplitude/power of each receive-beam before and after wall filtering, adding the amplitude/power of receive-beams from different acquisition-packages, estimating average threshold values from the summed amplitude/power information, and thresholding on high-resolution velocity information.

4. The system of claim 1, further comprising:
a power processor that determines a signal power of the structure flowing in the scan field flow from the RF-data.

5. The system of claim 4, further comprising:
a rendering engine that maps an output of the power processor to the desired display precision using a logarithmic (log)-based dynamic range compression with a control parameter range for an input dynamic range setting and a gain for an overall gain setting.

6. The system of claim 1, further comprising:
a variance processor configured to estimate a variance of the structure flowing in the scan field of view from the RF-data.

7. The system of claim 1, further comprising:
a vector-velocity processor configured to estimate a vector-velocity of the structure flowing in the scan field of view from the RF-data.

8. The system of claim 1, further comprising:
a vector-variance processor configured to estimate a vector-variance of the structure flowing in the scan field of view from the RF-data.

9. The system of claim 7, wherein the multiple synthetic transmit aperture beamformers include single-stage beamformers that process receive-channel echo-signals into receive-beams-groups of three receive-beams of RF-data, of which a receive-beam-pair is formed with a transverse oscillation, taking into account an estimated depth-dependent width of the transmit-beam, and wherein the vector-velocity processor interpolates and aligns decimated scan-lines with a lateral-velocity component to match a number of scan-lines with an axial-velocity component before displaying the vector-velocity information.

10. The system of claim 1, further comprising:
a preprocessor, including a high dynamic range color flow processor.

11. The system of claim 1, further comprising:
a spectral velocity Doppler processor configured to estimate an amplitude/power spectral density function from the RF data.

12. The system of claim 1, further comprising:
a spectral vector-velocity Doppler processor configured to estimate an amplitude/power spectral density function from the RF data.

13. The system of claim 1, further comprising:
a system controller configured to acquire sequences for at least one of non-package-interleaved imaging, package-interleaved imaging or package-interleaved imaging with continuous data per receive-beam location.

14. The system of claim 1, wherein the beamformers is a dual-stage synthetic transmit aperture beamformer.

15. A method, comprising:
transmitting, with a transducer array with a plurality of transducer elements, a pulsed field beam into a scan field of view;

receiving, with the transducer array, echo signals produced in response to the pulsed field interacting with particles/structure flowing/moving in the scan field of view;

generating, with the transducer array, electrical signals indicative of the echo signals;

processing, with a beamformer including multiple synthetic transmit aperture beamformers, the electrical signals over a plurality of processing channels into corresponding receive-beams of RF-data with a beam-level delay, channel-level delays, a beam-level gain and channel-level gains;

estimating, with a velocity processor, a velocity of the particles/structure flowing/moving in the scan field of view from the RF-data; and displaying, with a rendering engine, the flow velocity estimate on a display with color-coding.

16. The method of claim 15, wherein the beamforming includes only single-stage beamforming in which the channel-level delays and beam-level delays are applied once and summed in a single stage.

17. The method of claim 15, wherein the beamforming includes multi-stage beamforming in which channel-level delay-and-sum is performed in a first stage, intermediate RF-beams are buffered, and beam-level delay-and-sum is performed in a subsequent-stage.

18. A non-transitory computer readable medium encoded with computer readable instructions, which, when executed by a processor, cause the processor to:
transmit, via a transducer array with a plurality of transducer elements, a pulsed field beam into a scan field of view;

receive, via the transducer array, echo signals produced in response to the pulsed field interacting with particles/structure flowing/moving in the scan field of view;

generate, via the transducer array, electrical signals indicative of the echo signals;

process, with a beamformer including multiple synthetic transmit aperture beamformers, the electrical signals over a plurality of processing channels into corresponding receive-beams of RF-data with a beam-level delay, channel-level delays, a beam-level gain and channel-level gains;

estimate, with a velocity processor, a velocity of the particles/structure flowing/moving in the scan field of view from the RF-data; and display, with a rendering engine, the flow velocity estimate on a display with color-coding.

19. The non-transitory computer readable medium of claim 18, wherein the computer readable instructions cause the processor to employ only single-stage beamforming in which the channel-level delays and beam-level delays are applied once and summed in a single stage.

20. The non-transitory computer readable medium of claim 18, wherein the computer readable instructions cause the processor to employ multi-stage beamforming in which channel-level delay-and-sum is performed in a first stage, intermediate RF-beams are buffered, and beam-level delay-and-sum is performed in a subsequent-stage.

\* \* \* \* \*